United States Patent [19]

Higo et al.

[11] Patent Number: 4,819,753

[45] Date of Patent: Apr. 11, 1989

[54] FUNCTIONAL EVALUATION DEVICE CAPABLE OF EVALUATING AN ARTIFICIAL DEVICE BY THE USE OF ACOUSTIC EMISSION

[75] Inventors: Yakichi Higo, 5-3-1-101, Yagumo, Meguro-ku, Tokyo; Shigetomo Nunomura; Masashi Ono, both of Kawasaki, all of Japan

[73] Assignee: Yakichi Higo, Tokyo, Japan

[21] Appl. No.: 929,771

[22] Filed: Nov. 13, 1986

[30] Foreign Application Priority Data

Nov. 16, 1985 [JP] Japan ............................ 60-255851

[51] Int. Cl.$^4$ ............................................. A61B 7/00
[52] U.S. Cl. .................................. 128/773; 128/739; 73/587
[58] Field of Search ................ 128/715, 739, 773–774; 73/587, 801

[56] References Cited

U.S. PATENT DOCUMENTS

| | | | |
|---|---|---|---|
| 3,181,528 | 5/1965 | Brackin | 128/773 |
| 3,275,099 | 9/1966 | Speelman | 128/715 X |
| 3,682,161 | 8/1972 | Alibert | 128/715 X |
| 4,217,912 | 8/1980 | Hubmann et al. | 128/774 |
| 4,309,903 | 1/1982 | Ono | 73/801 X |
| 4,601,295 | 7/1986 | Teele | 128/746 |

FOREIGN PATENT DOCUMENTS

| | | | |
|---|---|---|---|
| WO85/04564 | 10/1985 | PCT Int'l Appl. | 128/773 |
| WO85/04563 | 10/1985 | PCT Int'l Appl. | 128/773 |
| 2096319 | 10/1982 | United Kingdom | 128/773 |

OTHER PUBLICATIONS

Chu et al; "A Noninvasive Electroacoustical Evaluation Technique of Cartilage Damage in Pathological Knee Jts."; *Med. & Biol. Eng. & Comput.*, 1978, 16, 437–442.

Ouellette; "TMJ Sound Prints", *J. of the Amer. Dental Assoc.*, vol. 89, 9-1974, pp. 623–628.

Primary Examiner—Kyle L. Howell
Assistant Examiner—Angela D. Sykes
Attorney, Agent, or Firm—Burns, Doane, Swecker & Mathis

[57] ABSTRACT

In a functional evaluation device for use in evaluating functional degradation of an artificial device buried in a living body, frequency zones of acoustic emission are detected by the use of the fact that the functional degradation brings about variation of the frequency zones. The acoustic emission may be measured at two different positions adjacent to the artificial device so as to detect an arrival time difference of the acoustic emission and to thereby locate the functional degradation. The acoustic emission is therefore picked up by a pair of transducers placed at the two positions and is processed by a processing circuit for detecting whether or not the functional degradation takes place and by a determining circuit for locating the functional degradation.

8 Claims, 8 Drawing Sheets $$V \times \Delta t = l_2 - l_1$$

sound velocity : V
arrival time difference : $\Delta t$

FUNCTIONAL EVALUATION DEVICE CAPABLE OF EVALUATING AN ARTIFICIAL DEVICE BY THE USE OF ACOUSTIC EMISSION

BACKGROUND OF THE INVENTION

This invention relates to a functional evaluation device for evaluating an artificial device, such as an artificial joint.

Various kinds of artificial devices have been recently manufactured and put into practical use. As one of the artificial devices, an artificial joint is proposed which comprises a joint element of metal, ceramics, or plastics The joint element may be a coated metallic element coated with ceramics or the like. An artificial hip joint will be exemplified as such an artificial joint hereinafter. The artificial hip joint is buried between two pieces of bones in a living body, such as human body, to join two pieces of bones together and to thereby restore normal activity of the living body. In this case, the artificial hip joint must be buried in the living body so as not to harm a motion of a patient as far as possible.

To this end, such an artificial hip joint is fixed at both ends thereof to the pelvis and the femur without any cement. The artificial hip joint resorts to ingrowth or regeneration of the bones adjacent to the artificial hip joint. Such ingrowth of the bones brings about cohesion between the artificial hip joint and the bones and is effective to firmly fix the artificial hip joint to the bones.

In practical use, it happens that the artificial hip joint is excessively sunk into a femur of a patient, which may be called "sinking" hereinafter. In addition, the artificial hip joint often becomes loose due to a crevice between the femur and the artificial hip joint, which may be referred to as "loosening." Such sinking and loosening weaken the cohesion between the artificial hip joint and the bones and give rise to functional degradation of the artificial hip joint. On occurrence of such functional degradation, the artificial hip joint must be superseded by a new one by a surgical operation. The surgical operation is painful for the patient physically and economically and thus, it would be desirable to find a way to avoid the need for such an operation.

It has been found out that the cohesion between the bones and the artificial hip joint can be recuperated without a surgical operation by a rest cure even after occurrence of the functional degradation, if the sinking and the loosening are discovered in their early stages. Therefore, it is important to early detect the functional degradation.

At present, such detection of sinking and loosening of the artificial hip joint must depend on consciousness of the patient, X-ray inspection, and motor function inspection. This means that the functional degradation of the artificial hip joint is detected and evaluated by relying on subjectivity of a patient and/or a doctor. However, such detection of the sinking and the loosening is not always easy for the patient and the doctor. Therefore, discovery of such sinking or loosening is liable to be too late to recuperate the sinking or the loosening by a rest cure. Under the circumstances, it is preferable that the sinking and loosening can be detected and evaluated with objectivity.

SUMMARY OF THE INVENTION

It is an object of this invention to provide a functional evaluation device which is objectively capable of evaluating functional degradation which might occur in relation to an artificial device.

It is another object of this invention to provide a functional evaluation device of the type described, which can be contributed to early discovery of the functional degradation.

It is still another object of this invention to provide a functional evaluation device of the type described, which is capable of locating sinking and loosening of the artificial device.

A functional evaluation device for evaluating an artificial device to which this invention is applicable is buried in a living body to restore a normal activity of the living body and causes acoustic emission of a frequency domain to occur in response to action of the living body. According to this invention, the functional evaluation device comprises sensing means for detecting, outside of the living body, the acoustic emission in response to the action of the living body, and processing means for processing the acoustic emission in the frequency domain to analyze functional degradation of the artificial device.

According to an aspect of this invention, the artificial device comprises a pair of ends and an intermediate portion between the ends. The acoustic emission travels along the artificial device towards the ends in the form of first and second acoustic signals from a position at which the acoustic emission takes place. The sensing means comprises first and second sensors which are to be placed adjacent to the ends outside of the living body for detecting the acoustic emission by receiving the first and the second acoustic signals, respectively. The functional evaluation device further comprises determining means coupled to the first and the second sensors for determining location of generation of the acoustic emission by detecting a time difference between the first and the second acoustic signals.

PRINCIPLES OF THE INVENTION

The present inventors' consideration has been directed to acoustic emission emitted from a living body, namely, a human body in response to action or motion thereof. According to the inventors' experimental studies, it has been found out that the acoustic emission is varied from normal emission in dependency upon functional degradation, such as sinking, loosening, of an artificial hip joint and that the functional degradation can be detected and located by monitoring the acoustic emission.

In order to prove such a fact, acoustic emission was measured about patients having the artificial hip joints and about non-patients having no artificial hip joints. Such measurement was made by making the patients and the non-patients take various forms of leg movements. As a result, acoustic emission was detected from the patients which was not detected from the non-patients. This shows that peculiar acoustic emission exits as to the artificial hip joint. Therefore, description will be made about the patients hereinafter.

Figure 1:
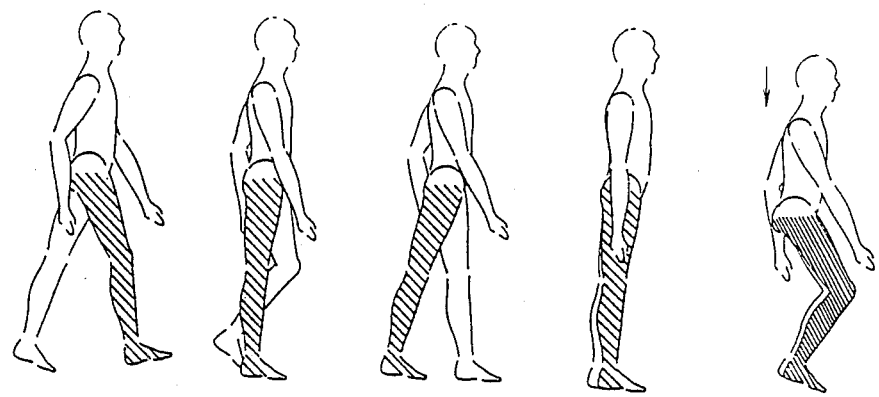
FIG. 1 shows eight movement forms from which acoustic emission is desired to detect and locate functional degradation in accordance with principles of this invention.
Figure 1:
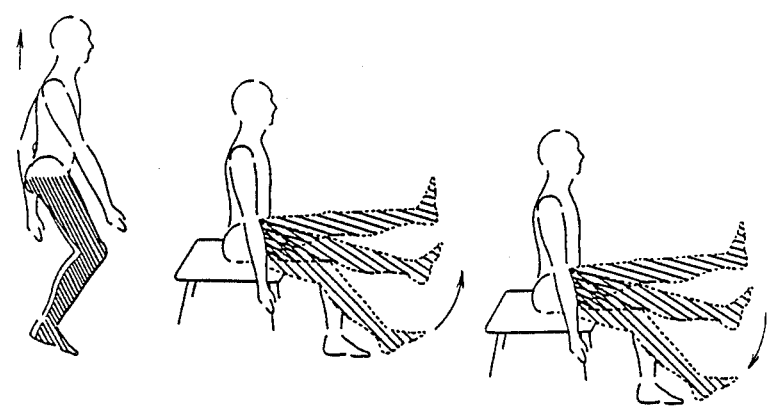

Referring to FIG. 1, the acoustic emission was measured when each of the patients and the non-patients took forms of leg movements, as illustrated in FIG. 1. FIG. 1 exemplifies the leg movements of a certain patient having an artificial hip joint buried in the shaded leg illustrated in FIG. 1. The forms of leg movements will simply be called movement forms and are numbered from No. 1 to No. 8 in FIG. 1. The movement forms Nos. 1 to 4 show walking action which will be named "walking" while the movement forms Nos. 5 and 6 show sitting down action and standing up action which will be named "sitting down" and "standing up," respectively. The movement form No. 1 may be called "stepping." The movement forms Nos. 7 and 8 show lifting action and lowering action which lift up and lower a leg with the patient sit down on a chair and which will be named "lifting" and "lowering," respectively.

Figure 2:
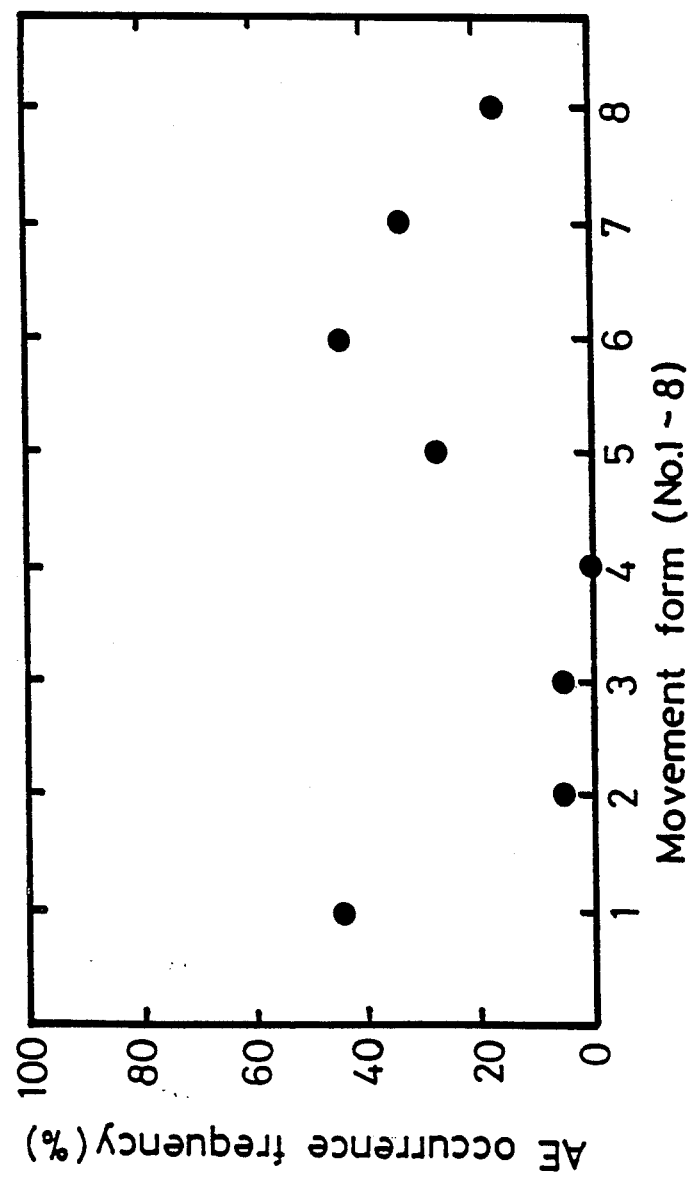
FIG. 2 shows a graph for use in describing a relationship between an occurrence frequency in acoustic emission and the movement forms illustrated in FIG. 1.

Referring to FIG. 2, the abscissa and the ordinate represent the movement forms and an AE occurrence frequency (%), namely, an occurrence frequency of the acoustic emission (AE). In this figure, it is clear that the acoustic emission occurs frequently in the movement forms Nos. 1, 5, 6, and 7 which correspond to the movement forms of "stepping," "sitting down," "standing up," and "lifting," respectively.

Figure 3:
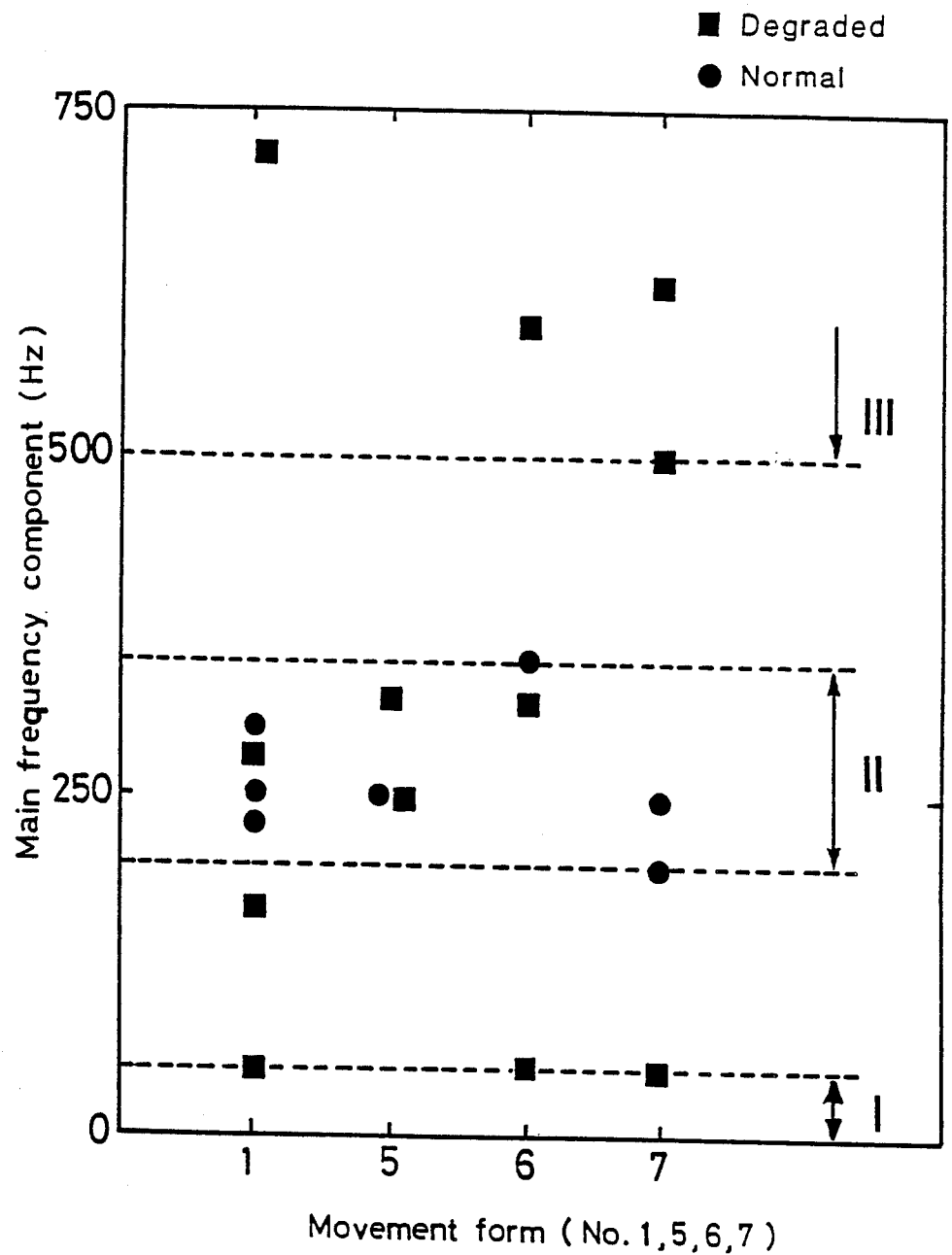
FIG. 3 shows a graph for use in describing a relationship between a main frequency component of the acoustic emission and the movement forms illustrated in FIG. 1.

Referring to FIG. 3, the abscissa and the ordinate represent the movement forms (Nos. 1, 5, 6, and 7) and a main frequency component (Hz) of the acoustic emission, respectively. In this figure, black square marks represent the acoustic emission which was emitted when the artificial hip joints were degraded while black circles represent the acoustic emission which appeared when the artificial hip joints were normal. In this event, degraded and normal states of the artificial hip joints were judged by X-ray inspection for the purpose of comparison.

As shown in FIG. 3, it has been confirmed that the main frequency components of the acoustic emission are distributed to three separated frequency ranges which will be called first, second, and third frequency zones I, II, and III hereinunder, when the artificial hip joints are buried in human bodies. The first, second, and third frequency zones I, II, and III are 50 Hz or lower, between 200 Hz and 350 Hz, and 500 Hz or higher, respectively. It is clear from FIG. 3 that the main frequency components of the acoustic emission are present in only in the second frequency zone II regardless of the movement forms when the artificial hip joints are in the normal state. When the artificial hip joints are in the degraded state, the main frequency components are present not only in the second frequency zone II but also in the first and the third frequency zones I and III. It is therefore possible to detect whether or not each artificial hip joint is normal or degraded by monitoring the acoustic emission in a frequency domain between 0.1 Hz and 2 kHz. In other words, it is possible to detect the functional degradation when the artificial hip joints are degraded. By the way, the functional degradation of the artificial hip joint can be divided into "sinking" and "loosening" as mentioned before.

According to the present inventors' experimental studies, it has been found out that the functional degradation of the artificial hip joints can be located by making use of the acoustic emission. More particularly, such location of the functional degradation is possible by monitoring the acoustic emission at two positions between which the artificial hip joints are interposed and by detecting an arrival time difference of the acoustic emission between the two positions. For this purpose, a sound velocity of the acoustic emission is measured at first in a bone.

Figure 4:
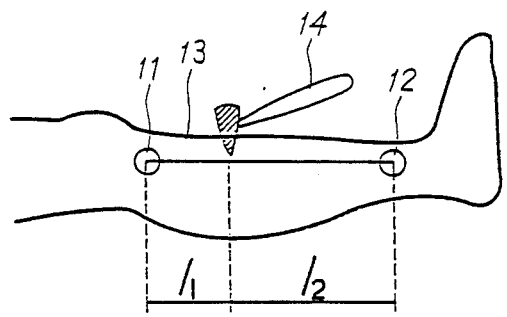
FIG. 4 shows a method of measuring a sound velocity of the acoustic emission in bone so as to describe a principle of this invention.

Referring to FIG. 4, two AE (acoustic emission) transducers 11 and 12, which will later be described more in detail, are attached to a leg 13, to detect acoustic emission. A distance of 20 cm is left between the two AE transducers 11 and 12. A leg bone is interposed between the two AE transducers 11 and 12. If acoustic emission is generated at a center portion of the two AE transducers 11 and 12, the acoustic emission is directed towards the AE transducers 11 and 12 and concurrently arrives at the two AE transducers. In addition, if the acoustic emission takes place at a position which is spaced apart from the AE transducer 11 by $l_1$ and from the AE transducer 12 by $l_2$, the arrival time difference $\Delta t$ is given by:

$$V \cdot \Delta t = l_2 - l_1,$$

where V is representative of the sound velocity in bone. Herein, the arrival time difference $\Delta t$ can be measured from the detected signals. Under the circumstances, an intermediate portion of the leg bone between the AE transducers 11 and 12 was hit by a hammer, as shown in FIG. 4. In order to achieve a higher precision, a cross correlation function was additionally used between the detected signals. As a result, the sound velocity V in bone was found to be appreciably slow, about 200 m/s, despite transmission of a sound wave through a solid.

Figure 5:
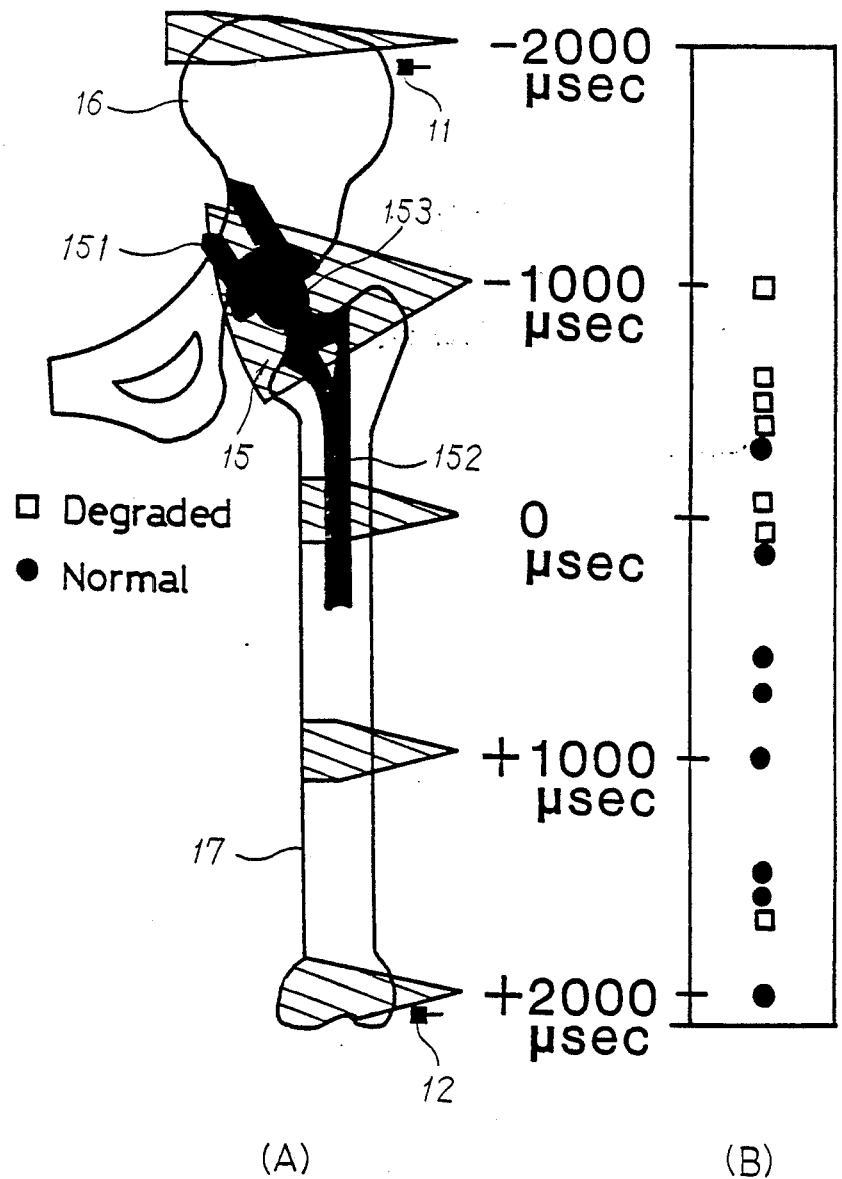
FIGS. 5(A) and 5(B) roughly show a bone structure and an arrival time difference of acoustic emission to locate functional degradation.

Referring to FIG. 5(A), description will be made about locating the functional degradation of the artificial hip joint 15 in consideration of the sound velocity V in bone. The illustrated artificial hip joint 15 is mounted between a pelvis 16 and a femur 17. The artificial hip joint 15 comprises a socket portion 151 fixed in the pelvis 16. A stem portion 152 is inserted into the femur 17. The socket portion 151 and the stem portion 152 are connected to each other through a universal ball joint 153.

The two transducers 11 and 12 are mounted outside of a spina iliaca posterior superior of the pelvis 16 and outside of a condylus lateralis of the femur 17, respectively. These positions of the transducers 11 and 12 are close to the bones. Accordingly, movements of muscle and skin can be reduced in these positions to a relatively small range. Therefore, the above-mentioned positions are helpful for avoiding attenuation of the acoustic emission.

Figure 6:
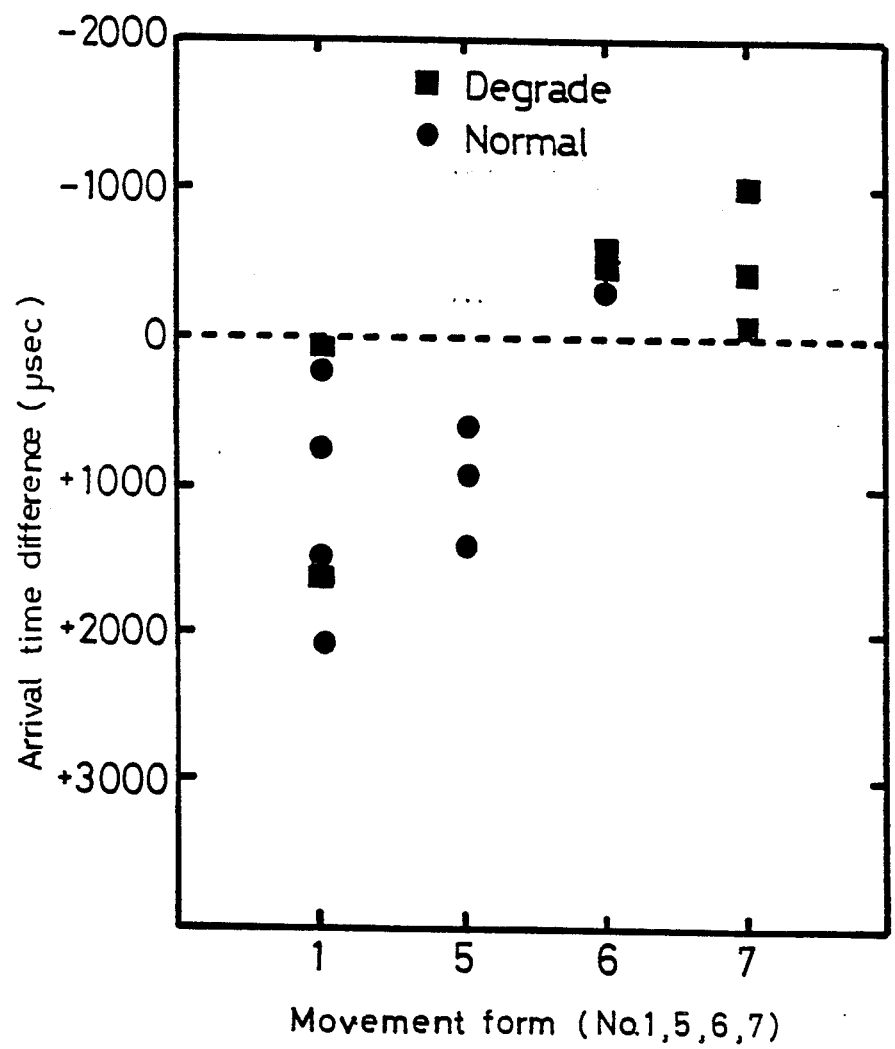
FIG. 6 shows a graphical representation for use in describing the arrival time difference and the movement forms.

Referring to FIG. 6, the abscissa and the ordinate represent the movement forms (Nos. 1, 5, 6, and 7) and the afore-described arrival time difference Δt in microsecond. In this figure, each black square mark represents a result of measurement derived from a degraded one of the artificial hip joints. Each black circle mark represents a result of measurement derived from a normal one of the artificial hip joints. The transducers 11 and 12 are mounted in a manner as in FIG. 5. Negative values of the arrival time difference represent that the AE transducer 11, namely, pelvis side transducer 11 first detects the acoustic emission before the acoustic emission is received by the transducer 12, namely, knee side transducer. On the contrary, positive values of the arrival time difference represent that the knee side transducer 12 detects the acoustic emission faster than the pelvis side transducer 11. In the manner described earlier, the sound velocity is appreciably slow in the bone. On the other hand, it is well known that the acoustic emission travels very fast through metallic parts, such as the artificial hip joint. Therefore, presence of the metallic parts may be assumed to be neglected. In other words, consideration may be directed only to the sound velocity V in bone.

Referring to FIG. 5(B), location of generation of the acoustic emission is estimated with reference to the sound velocity of the acoustic emission in the bone. In this figure, each open square mark shows a result of measurement obtained when each artificial hip joint is degraded. Each black circle mark shows a result of measurement obtained when each artificial hip joint is normal. It is evident that almost all of the open square marks are at or near the artificial hip joint 15 and may therefore specify degraded positions at which "sinking" or "loosening" takes place. Such square marks can be assumed to attribute to the functional degradation. Therefore, it is possible to locate functional degradation of the artificial hip joint by detecting the arrival time difference.

DESCRIPTION OF THE PREFERRED EMBODIMENT

Figure 7:
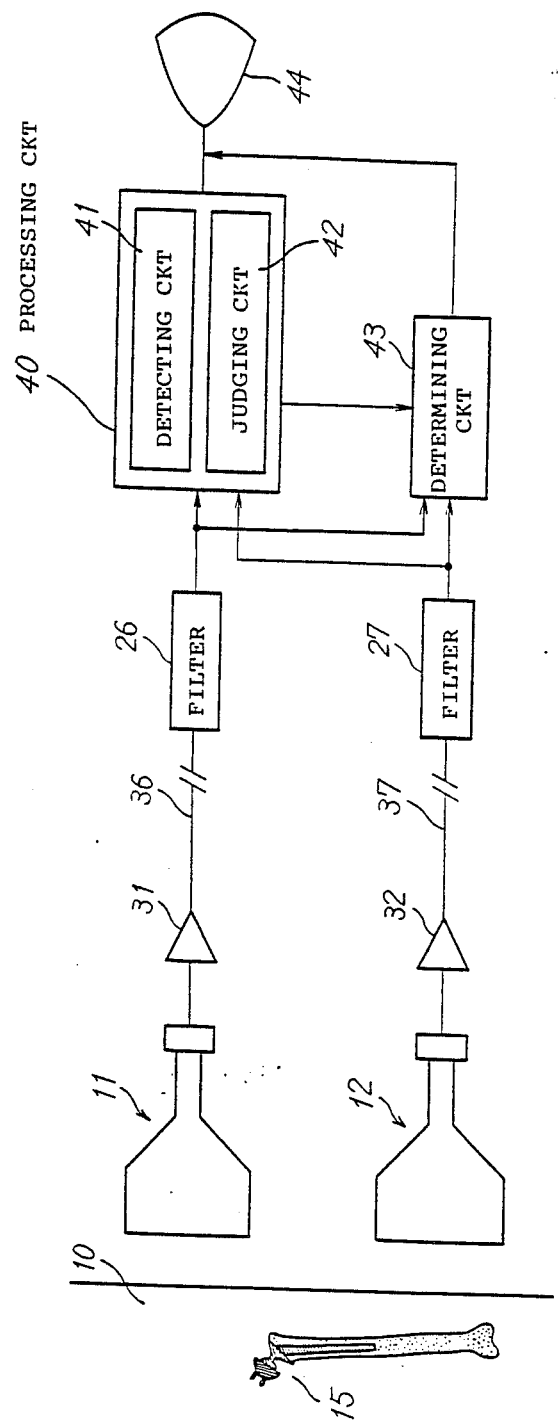
FIG. 7 is a block diagram of a functional evaluation device according to an embodiment of the present invention.

Referring to FIG. 7, a functional evaluation device according to an embodiment of the present invention includes two AE transducers 11 and 12 for detecting acoustic emission in response to action or movements of a patient (a living body) 10 in which an artificial hip joint 15 is buried to restore a normal activity of the patient 10. The acoustic emission is appreciably and rapidly attenuated at an especially high frequency component in the body while a low frequency component of the acoustic emission is propagated through the body 10. Therefore, the AE transducers 11 and 12 pick up the acoustic emission which consists of an audio frequency range from 1 Hz to 1 kHz through the skin. The transducer must be conveniently and reliably mounted on the skin and should eliminate outside noise such as fretting or rubbing noise with the skin.

Figure 8:
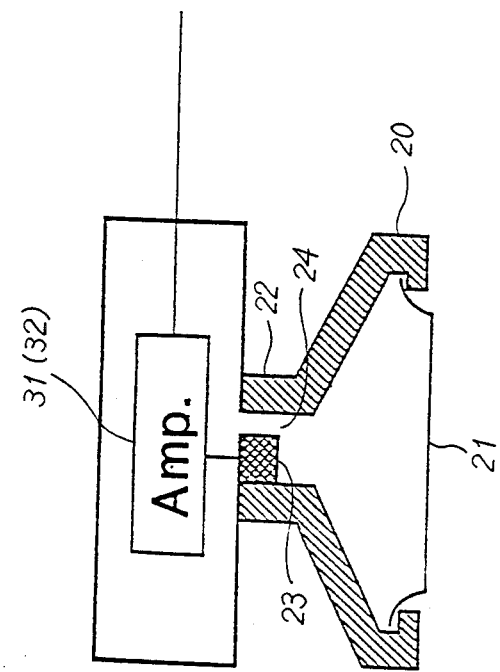
FIG. 8 is a schematic longitudinal sectional view of an AE (acoustic emission) transducer for use in the functional evaluation device illustrated in FIG. 7.

Turning to FIG. 8, the transducer 11 modifies a stethoscope. The transducer 12 is similar in structure to the transducer 11. Each transducer 11 comprises a conical resonance body 20 of stainless steel. The conical resonance body 20 has an aperture at a wide end portion thereof. The aperture is covered with a resin film 21 which is to be brought into contact with the skin of the body 10. The resin film 21 converts the acoustic emission in the body 10 into air vibration. A pipe 22 is connected to a narrow end portion of the conical resonance body 20. A condenser microphone 23 is mounted on a portion of an inside pipe wall of the pipe 22 by a suitable adhesive, such as silicone rubber. An air ventilation hole 24 is left between the condenser microphone 23 and the inside pipe wall portion whereon the microphone 23 is not mounted. The air ventilation hole 24 is for eliminating a signal having an ultra low frequency and a larger amplitude due to pulse of the body 10.

A cream is applied to the skin before mounting the transducer in order to eliminate the fretting noise between the transducer and the skin. The cream may be keratin cream which is used in an electrocardiogram measurement. The transducer is fixed on the skin by the help of an elastic tape or the like.

For measurement of the acoustic emission, the AE transducers 11 and 12 should be mounted on a portion where movement of muscle and skin is not transmitted directly. In this connection, the AE transducers 11 and 12 are preferably close to a bone to avoid that attenuation of the acoustic emission which might occur due to the movement of muscle and skin. Under the circumstances, the above-mentioned two positions adjacent to a pelvis 16 and a knee 17 are selected so as to mount the AE transducers 11 and 12, respectively, as shown in FIG. 5(A).

Turning back to FIG. 7, the microphones, such as 23, in the transducers 11 and 12 convert the acoustic emission into two electrical signals which are transmitted to filters 26 and 27 through amplifiers 31 and 32 and cables 36 and 37, respectively. The filters 26 and 27 eliminate noise in the electrical signals to produce first and second filtered signals, respectively. The first and the second filtered signals are delivered from the first and the second filters 26 and 27 to a processing circuit 40. The processing circuit 40 selects one of the first and the second filtered signals that has a larger amplitude than the other. For this purpose, the processing circuit 40 comprises a selector (not shown) for selecting a larger one of the first and the second filtered signals as a selected filtered signal. The selected filtered signal is processed in a frequency domain to analyze functional degradation of the artificial hip joint.

The processing circuit 40 comprises a detecting circuit 41 responsive to the selected filtered signal. The detecting circuit 41 detects where the first filtered signal falls within the first, second, and third frequency zones I, II, and III (FIG. 3) of the frequency domain. The detecting circuit 41 produces first, second, and third detection signals when the filtered signal falls within the first through the third frequency zones I through III, respectively. The detecting circuit 41 may comprise an FFT (Fast Fourier Transformation) analyzer.

The processing circuit 40 further comprises a judging circuit 42 coupled to the detecting circuit 41. The judging circuit 42 judges the artificial hip joint 15 normal only when the second detection signal alone is supplied from the detecting circuit 41. Otherwise, the judging circuit 42 judges the artificial hip joint 15 to be put into the functional degradation. Anyway, a first result of processing is produced from the judging circuit 42.

The first and second filtered signals are delivered from the filters 26 and 27 to a determining circuit 43, respectively. The determining circuit 43 may be placed in the processing circuit 40 and is for determining a position of generation of the acoustic emission in the above-mentioned manner by detecting an arrival time difference between the filtered signals with reference to the sound velocity of 200 m/s. A second result of processing is produced from the determining circuit 43 with reference to the first result of processing given from the processing circuit 40.

The first and the second results of processing are displayed on a display device 44, such as CRT (Cathode Ray Tube).

While the present invention has thus far been described in conjunction with a preferred embodiment thereof, it will readily be possible for those skilled in the art to put this invention into practice in various other manners. For example, the artificial device may be an artificial bone and so on. The living body may be an animal. The acoustic emission detected by the transducers may be recorded in a video tape together with pictures of the patients' movement taken by a camera. In addition, the first and the second results of processing may be sent from he judging circuit 42 and the determining circuit 43 through a transmission line to a central station for analyzing the first and the second results. This means that a value-added network (VAN) can be formed to diagnose the artificial device.

What is claimed is:

1. A functional evaluation apparatus for evaluating the functional condition of an artificial joint buried in a living body which generates an inherent acoustic emission, the presence of the artificial joint causing the occurrence of an additional acoustic emission in response to each of a plurality of different movement forms of the living body, said additional acoustic emission having an acoustic frequency domain which is peculiar to the artificial joint and which is higher than the acoustic frequency domain of said inherent acoustic emission, the acoustic frequency domain for a properly functioning artificial joint differing from that of an improperly functioning artificial joint for each said movement form, said apparatus comprising:

first and second sensors, each of said sensors comprising a resonance body having a first and second oppositely positioned open ends, the first open end of each sensor having a pipe portion attached thereto and extending therefrom, the second open end of each sensor having a film attached thereto for converting the inherent acoustic emissions and the additional acoustic emissions into air vibration within said resonance body;

transducing means mounted inside the pipe portion of each sensor, with an air ventilation hole being provided within said pipe portion, for transducing said air vibration into an electrical signal with a component of said inherent acoustic emission removed from said electric signal, said electrical signal having a frequency domain corresponding to the frequency domain of said additional acoustic emission; and frequency analyzing means coupled to said first and second sensors for analyzing the frequency domain of said electic signal to judge whether or not said artificial joint is properly functioning.

2. A functional evaluation apparats according to claim 1, wherein said frequency analyzing means comprises detecting means for detecting three frequency zones of the frequency domain of a selected on of the electrical signals, said three frequency zones comprising a first frequency zone, a second frequency zone higher than said first frequency zone, and a third frequency zone higher than said second frequency zone, said detecting means including means for generating first, second, and third detection signals corresponding to detected frequencies in said first, second and third frequency zones respectively, said frequency analyzing means comprising means for judging that the artificial joint is properly functioning when only said second detection signal is generated by said detecting means and for judging that the artificial joint is improperly functioning when any other detection signal is generated by said detecting means.

3. A functional evaluation apparatus as claimed in claim 1, wherein said second frequency zone extends from 200 to 350 Hz.

4. A functional evaluation apparatus according to claim 1, wherein the artificial joint comprises a pair of joint ends and an intermediate portion located between said joint ends, said additional acoustic emission traveling along the artificial joint towards said joint ends in the form of a first and second acoustic signals from a position at which said additional acoustic emission takes place, said first and second sensors being adapted to be placed outside of the living body adjacent to said joint ends for receiving said first and second acoustic signals to thereby produce said electric signals, said functional evaluation apparatus further comprising determining means coupled to said first and second sensors for determining the position of generation of said additional acoustic emission by detecting an arrival time difference between said first and second acoustic signals at said joint ends.

5. A functional evaluation apparatus according to claim 4, wherein said determining means determines the position of generation of said additional acoustic emission by monitoring the first and second acoustic signals, each of which has a sound velocity of 200 m/s.

6. A functional evaluation apparatus as claimed in claim 4, said acoustic emission being transmitted through said living body at a predetermined sound velocity, wherein said determining means determines said position with reference to said predetermined sound velocity.

7. A functional evaluation apparatus as claimed in claim 4, wherein said determining means detects said time difference by using a cross correlation function between said first and said second acoustic signals.

8. A functional evaluation apparatus as claimed in claim 4, said artificial joint being an artificial hip joint which is to be mounted between a pelvis and a femur, wherein said first sensor is adapted to be mounted on a spina iliaca posterior superior of said pelvis, and said second sensor is adapted to be mounted on the outside of a condylus lateralis of said femur.

* * * * *